United States Patent [19]
Baillet et al.

[11] Patent Number: 5,948,760
[45] Date of Patent: Sep. 7, 1999

[54] THERAPEUTIC USE OF SUPEROXIDE DISMUTASES

[75] Inventors: François Baillet; Ioannis Lamproglou, both of Paris, France

[73] Assignee: Assistance Publique-Hopitaux De Paris, Paris, France

[21] Appl. No.: 08/849,699

[22] PCT Filed: Nov. 29, 1995

[86] PCT No.: PCT/FR95/01579

§ 371 Date: Aug. 11, 1997

§ 102(e) Date: Aug. 11, 1997

[87] PCT Pub. No.: WO96/16670

PCT Pub. Date: Jun. 6, 1996

[30] Foreign Application Priority Data

Nov. 30, 1994 [FR] France ................................. 94 14354

[51] Int. Cl.⁶ .................................................. A61K 38/43
[52] U.S. Cl. ........................................................ 514/12
[58] Field of Search ................................................ 514/12

[56] References Cited

FOREIGN PATENT DOCUMENTS 0289 667 A1  11/1988  European Pat. Off. .

OTHER PUBLICATIONS

Roda et al, Chemical Abstracts, vol. 115, abstract No. 247753, 1991.

Kizuki et al, Biological Abstracts, vol. 92, abstract No. 44946, 1991.

Matsumiya et al, Chemical Abstracts, vol. 115, abstract No. 247930, 1991.

Uyama et al, Chemical Abstracts, vol. 116, abstract No. 143724, 1992.

"Superoxide Dismutase and Catalase as Therapeutic Agents for Human Diseases—A Critical Review", Greenwald, Robert A., *Free Radical Biology & Medicine,* vol. 8, No. 2, pp. 201–209, 1990.

"Age–related changes in levels of the β–subunit of nerve growth factor in selected regions of the brain: comparison between senescence–accelerated (SAM–P8) and senescence–resistant (SAM–R1) mice", Katoh–Semba et al., Neuroscience Research, vol. 20, No. 3, pp. 251–256, 1994.

Database WPI, Section Ch, Week 9433, Derwent Publications Ltd., London GB; Class B05, AN 94–269367 & JP,A,06 199 690 (Kato K), Jul. 19, 1994.

*Primary Examiner*—William R. A. Jarvis
*Attorney, Agent, or Firm*—Morgan, Lewis & Bockius LLP

[57] ABSTRACT

A method is disclosed for treating or preventing cognitive brain function disorders following cerebral damage or injury by administration of a preparation of human superoxide dismutase.

13 Claims, 1 Drawing Sheet

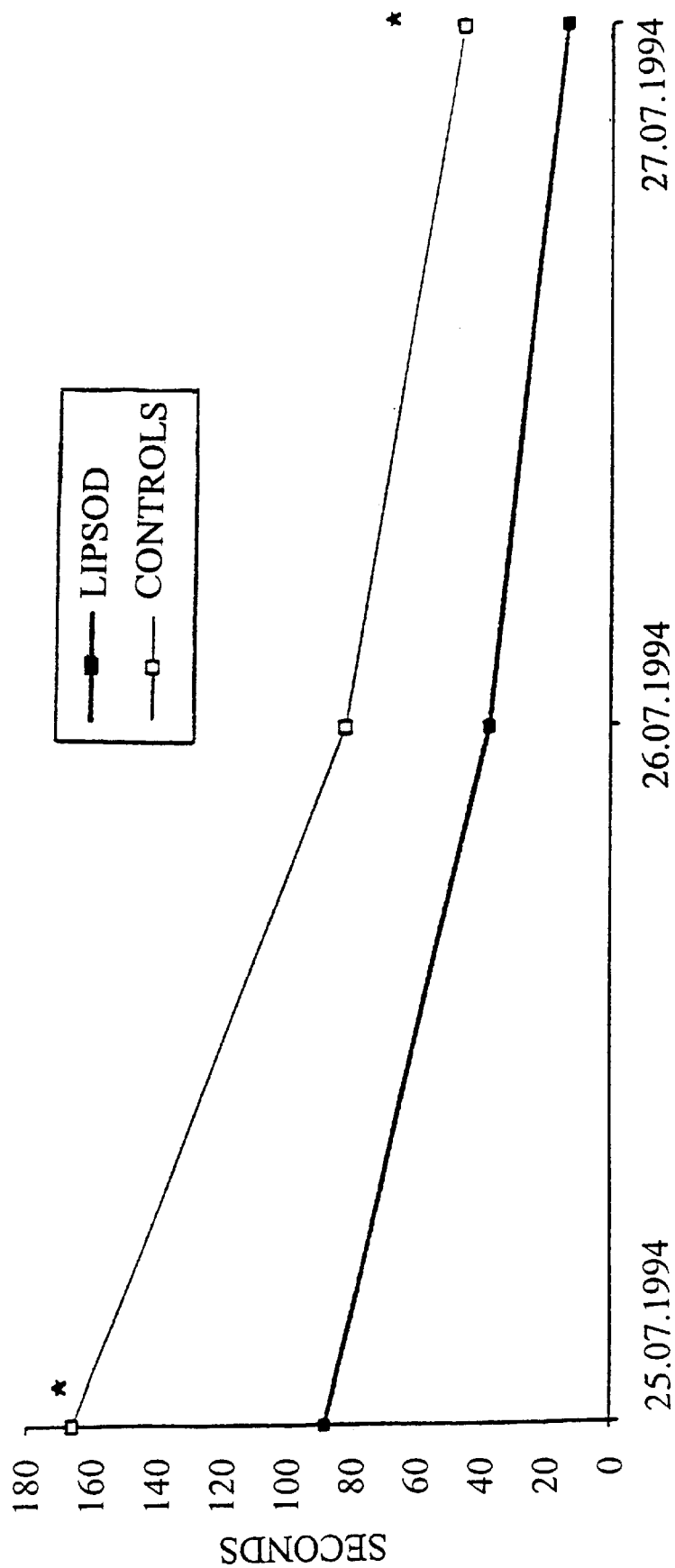

THERAPEUTIC USE OF SUPEROXIDE DISMUTASES

This application is a 371 of PCT/FR95/01579, filed Nov. 29, 1995.

FIELD OF THE INVENTION

The present invention relates to a novel therapeutic use of superoxide dismutases (SOD).

BACKGROUND

SOD was characterized in 1968 by McCORD and FRIDOVICH; it is an enzyme which promotes removal of the superoxide radical ($O_2^-$), constitutes a priori a mechanism of protection against the deleterious effects of this radical, is capable of being formed in vivo from atmospheric oxygen and therefore plays a major role in preventing the toxic effects which could result from exposure to an oxygenated atmosphere.

As free radicals derived from oxygen seem to be involved in numerous complaints, the use of SOD in therapeutics has therefore been recommended in inflammatory arthropathy (R. NORDMANN et al., Cah. Nutr. Diet., 1991, 26, 6, 398–402); SOD has also been proposed with a greater or lesser degree of success in pulmonary diseases, more particularly bronchopulmonary dysplasia, or in other toxic conditions associated with the presence of substantial amounts of oxygen (central nervous system, ischaemia, non-vascular gastro-intestinal disorders, ocular disorders (locally in the anterior chamber of the eye) or control of the undesirable effects of anticancer treatments) (GREENWALD R. A., Free Radical Biol. Med., 1990, 8, 201–209).

SOD, in its liposomal bovine Cu/Zn form, has been found to be particularly effective on radiofibrosis in clinical trials (Baillet F. et al., Treatment of radiofibrosis with liposomal superoxide dismutase. Preliminary results of 50 cases, Free Rad. Res. Commun., 1, 387–394, Harwood Academic Publishers GmbH, 1986) and subsequently in experiments on pigs (Lefaix J. L. et al., La fibros cutanéo-musculaire radio-induite: efficacité thérapeutique majeure de la SOD Cu/Zn liposomiale (Radioinduced cutaneomuscular fibrosis: major therapeutic efficacy of liposomal Cu/Zn SOD), Bull. Cancer, 1993, 80, 799–807), these results being all the more interesting because there is no product which has an equivalent action.

Of the SODs tested, those which have an extended half-life and a low incidence of immunological illnesses are preferred; the following may be mentioned in particular: Cu/Zn SOD of bovine origin (a homodimer which catalyses the dismutation of the superoxide radical), Mn SOD, Fe SOD, liposomal SODs, SODs conjugated with polyethylene glycol, SOD polymers or copolymers and recombinant human Cu/Zn SOD and Mn SOD.

SUMMARY OF THE INVENTION

The Applicants have found a novel use of SOD-based preparations with an extended duration of action for the production of a drug intended for treating or preventing brain function disorders, preferably cognitive brain function disorders, which are caused by a specific cerebral aggression, damage, stress or insult or by a non-specific aggression.

In terms of the present invention, non-specific aggression is understood as meaning for example an electrical stimulation (plantar shock) and specific cerebral aggression, damage, stress or insult, is understood as meaning for example extended whole-head irradiation.

Unexpectedly, the said SOD preparation with an extended duration of action protects mammals from brain function disorders in both a preventive capacity and a curative capacity.

The SOD preparation with an extended duration of action is preferably selected especially from liposomal SODs, SOD/polyethylene glycol conjugates and SOD polymers or copolymers.

Advantageously, the superoxide dismutase (SOD) is especially mammalian (murine, bovine, human) Cu/Zn SOD, Mn SOD or Fe SOD or a recombinant SOD.

These preparations can be administered either parenterally, preferably subcutaneously, or orally.

The SOD-based preparations as defined above can be used in mammals, and especially in man, for the curative or preventive treatment of the cognitive brain function disorders caused by a specific cerebral aggression, damage, stress or insult, (for example irradiation) or by a non-specific aggression (for example electrical stimulation).

The doses of SOD are effective on the complications of radiotherapy over a wide range of posologies, the extremes going from 2.3 mg/kg in pigs to 0.03 mg/kg in man. In man, the prescribed daily dose will preferably be between 0.03 mg/kg and 0.08 mg/kg, administered subcutaneously.

Apart from the foregoing provisions, the invention also comprises other provisions which will become apparent from the following description referring to examples of how to carry out the process forming the subject of the present invention.

It must be clearly understood, however, that these examples are given solely in order to illustrate the subject of the invention without in any way implying a limitation.

BRIEF DESCRIPTION OF THE DRAWING

FIG. 1 presents the results of a two-way avoidance test, showing that the rats decreased their exposure times to electric shock following treatment with liposomal Cu/Zn SOD.

EXAMPLE 1

Preventive Effect of an SOD Treatment on a Non-specific Aggression (Electrical Stimulation)

Aggression: electrical stimulation

The intensity of the plantar shock above a certain threshold (1.1 to 1.2 mA) strongly inhibits the appearance of the conditioned response (avoidance). In the following study, plantar shocks of 1.5 mA were applied, the usual conditions being 0.8 mA.

Methods and Equipment

Animals 12 five-month-old male rats of the Wistar strain are randomly divided into 2 groups of six: 1) a control group and 2) a liposomal Cu/Zn SOD group.

Treatment 2 hours before each training session, 0.5 mg/kg of liposomal Cu/Zn SOD is administered subcutaneously to the liposomal Cu/Zn SOD group at a rate of 0.05 ml/100 g body weight. The control group received an equivalent volume of 0.9% NaCl.

Behavioural Test

Two-Way Avoidance

The animals have to move from a compartment A to another compartment B in order to avoid the electric shock (1.5 mA for 15 seconds) which is alternately applied either to the floor of cage A or to the floor of cage B. An audio conditioned stimulus (300 Hz) enables them to avoid this shock provided they react within a period of 6 seconds (duration of the conditioned stimulus and the interval). The training takes place over three consecutive days at a rate of one session per day. Each session is made up of 15 trials. The interval between the trials is 50 seconds. The number of avoidances, the number of failed escapes and the time of exposure to plantar shock are recorded.

Statistics

The raw individual data were used to calculate the mean values, the standard errors in the mean (sem), the group sizes and the Student t values. The comparisons are made between the two groups using all the results obtained.

Results

Percentage avoidance

The comparison between the control group and the liposomal Cu/Zn SOD group (Table I) shows a significant difference as from the first day of training in favour of the treated group (12.22% vs 0%, p=0.02). This difference persists to a lesser extent on the second day (14.44% vs 1.11%, p=0.15) and the third day (23.33% vs 4.45%, p=0.09).

Percentage of Failed Escapes

It is seen (Table II) that the treatment with liposomal Cu/Zn SOD significantly reduces the failed escapes on the first day (13.33% vs 58.88%, p=0.02) and that this reduction is maintained at a certain level on the second day of training (0% vs 14.45%, p=0.11).

Duration of exposure to plantar shock per session

The administration of liposomal Cu/Zn SOD (Table III, FIG. 1) enables the rats better to control the aggression due to the unconditioned stimulus (1.5 mA shock) since they reduce their shock exposure times significantly on the first day (88.93 sec vs 165.62 sec, p=0.04), on the third day (13.61 sec vs 45.64 sec, p=0.03) and to a certain extent on the second day of training (37.52 sec vs 82.50 sec, p=0.15). This suggests that during the course of the 15 trials which make up the session, liposomal Cu/Zn SOD acts effectively not only at the moment of shock but also during the rest period (50 sec) separating two consecutive trials.

Conclusion

The protective effect of liposomal Cu/Zn SOD is clear when considering the three parameters studied during the acquisition of two-way avoidance.

Unexpectedly, the administration of liposomal Cu/Zn SOD therefore reduces the adverse effects of a non-specific aggression (electrical stimulation) which interferes with the acquisition of training. In fact, prior subcutaneous injections of SOD enable the training capacity to be preserved.

TABLE I

TWO-WAY AVOIDANCE: percentage avoidance
PRELIMINARY TRIALS: EFFECT OF LIPSOD ON 5-MONTH-OLD MALE WISTAR RATS IN A NEGATIVE REINFORCEMENT TEST

| GROUP | Rat no. | 07.25.1994 | 07.26.1994 | 07.27.1994 |
|---|---|---|---|---|
| LIPSOD 0.5 mg/kg 2 h BEFORE S.C. | 7 | 13.33 | 0.00 | 20.00 |
| | 8 | 13.33 | 53.33 | 53.33 |
| | 10 | 0.00 | 0.00 | 0.00 |
| | 16 | 0.00 | 0.00 | 6.67 |
| | 17 | 20.00 | 13.33 | 6.67 |
| | 18 | 26.67 | 20.00 | 53.33 |
| | MEAN | 12.222 | 14.438 | 23.333 |
| | SEM | 4.361 | 8.501 | 9.850 |
| | N | 6 | 6 | 6 |

TABLE I-continued

TWO-WAY AVOIDANCE: percentage avoidance
PRELIMINARY TRIALS: EFFECT OF LIPSOD ON 5-MONTH-OLD MALE WISTAR RATS IN A NEGATIVE REINFORCEMENT TEST

| GROUP | Rat no. | 07.25.1994 | 07.26.1994 | 07.27.1994 |
|---|---|---|---|---|
| | Student t | 2.803 | 1.554 | 1.818 |
| | p | 0.018 | 0.151 | 0.099 |
| CONTROLS | 11 | 0.00 | 0.00 | 0.00 |
| | 12 | 0.00 | 0.00 | 0.00 |
| | 13 | 0.00 | 0.00 | 6.67 |
| | 15 | 0.00 | 6.67 | 20.00 |
| | 19 | 0.00 | 0.00 | 0.00 |
| | 20 | 0.00 | 0.00 | 0.00 |
| | MEAN | 0.000 | 1.112 | 4.445 |
| | SEM | 0.000 | 1.112 | 3.296 |
| | N | 6 | 6 | 6 |

TABLE II

TWO-WAY AVOIDANCE: percentage of failed escapes
PRELIMINARY TRIALS: EFFECT OF LIPSOD ON 5-MONTH-OLD MALE WISTAR RATS IN A NEGATIVE REINFORCEMENT TEST

| GROUP | Rat no. | 07.25.1994 | 07.26.1994 | 07.27.1994 |
|---|---|---|---|---|
| LIPSOD 0.5 mg/kg 2 h BEFORE S.C. | 7 | 13.33 | 0.00 | 0.00 |
| | 8 | 0.00 | 0.00 | 0.00 |
| | 10 | 26.67 | 0.00 | 0.00 |
| | 16 | 26.67 | 0.00 | 0.00 |
| | 17 | 6.67 | 0.00 | 0.00 |
| | 18 | 6.67 | 0.00 | 0.00 |
| | MEAN | 13.335 | 0.000 | 0.000 |
| | SEM | 4.555 | 0.000 | 0.000 |
| | N | 6 | 6 | 6 |
| | Student t | 2.654 | 1.734 | 1.225 |
| | p | 0.024 | 0.114 | 0.249 |
| CONTROLS | 11 | 100.00 | 46.67 | 0.00 |
| | 12 | 46.66 | 6.67 | 0.00 |
| | 13 | 80.00 | 0.00 | 6.67 |
| | 15 | 6.67 | 0.00 | 0.00 |
| | 19 | 20.00 | 0.00 | 0.00 |
| | 20 | 100.00 | 33.33 | 33.33 |
| | MEAN | 58.888 | 14.445 | 6.667 |
| | SEM | 16.548 | 8.329 | 5.442 |
| | N | 6 | 6 | 6 |

TABLE III

TWO-WAY AVOIDANCE: duration of exposure to plantar shock per session (in seconds)
PRELIMINARY TRIALS: EFFECT OF LIPSOD ON 5-MONTH-OLD MALE WISTAR RATS IN A NEGATIVE REINFORCEMENT TEST

| GROUP | Rat no. | 07.25.1994 | 07.26.1994 | 07.27.1994 |
|---|---|---|---|---|
| LIPSOD 0.5 mg/kg 2 h BEFORE S.C. | 7 | 65.00 | 27.42 | 11.67 |
| | 8 | 37.49 | 14.01 | 7.63 |
| | 10 | 127.16 | 34.14 | 18.80 |
| | 16 | 168.53 | 106.87 | 22.73 |
| | 17 | 72.45 | 26.70 | 13.00 |
| | 18 | 62.94 | 15.97 | 7.84 |
| | MEAN | 88.928 | 37.518 | 13.612 |
| | SEM | 19.970 | 14.209 | 2.472 |
| | N | 6 | 6 | 6 |
| | Student t | 2.365 | 1.536 | 2.434 |
| | p | 0.040 | 0.155 | 0.035 |
| CONTROLS | 11 | 225.00 | 180.86 | 39.18 |
| | 12 | 151.71 | 77.62 | 30.34 |
| | 13 | 204.58 | 47.93 | 61.47 |
| | 15 | 78.16 | 37.31 | 18.51 |
| | 19 | 109.28 | 18.04 | 22.19 |
| | 20 | 225.00 | 133.25 | 102.22 |
| | MEAN | 165.622 | 82.502 | 45.652 |

TABLE III-continued

TWO-WAY AVOIDANCE: duration of exposure to plantar shock per session (in seconds)
PRELIMINARY TRIALS: EFFECT OF LIPSOD ON 5-MONTH-OLD MALE WISTAR RATS IN A NEGATIVE REINFORCEMENT TEST

| GROUP | Rat no. | 07.25.1994 | 07.26.1994 | 07.27.1994 |
|---|---|---|---|---|
| | SEM | 25.552 | 25.604 | 12.928 |
| | N | 6 | 6 | 6 |

EXAMPLE 2
Cognitive Dysfunction Induced by Irradiation of the Head: Curative Effect of Liposomal Cu/Zn Super-oxide Dismutase in Rats Irradiated at the Age of 4 Months Methods and equipment Animals 15 male rats of the Wistar strain, irradiated at the age of 4 months, are divided into 2 groups: 1) a control group, n=7 and 2) a group treated with liposomal Cu/Zn SOD 9 months after irradiation, n=8.

Treatment

Once a day for five consecutive days, 0.5 mg/kg of liposomal Cu/Zn SOD is administered subcutaneously to the animals of group 2 at a rate of 0.05 ml/100 g body weight, while group 1 received an equivalent volume of 0.9% NaCl. Three days later and two hours before the behavioural test, a sixth injection of liposomal Cu/Zn SOD or 0.9% NaCl was given.

Irradiation (9 months before treatment):

The rats were anaesthetized with 250 mg/kg of chloral hydrate (i.p. administration) at a rate of 0.5 ml/100 g body weight. The rat's encephalon was treated with two equally weighted, opposite beams of radio-cobalt. The two beams were applied on the same day. A dose of 30 Gy was delivered in 10 fractions over 12 days on the basis of the isodose corresponding to 95% of the dose at the isocentre according to computer dosimetry. The buccal cavity, the snout, the eyes and the cervical spinal cord were protected by a 5 cm thick, customized lead mask placed near the point of entry through the skin. The distance between the cobalt 60 source and the axis is 80 cm. After irradiation, the rats were housed in their original cages (4 to 5 animals in each).

Behavioural Test

Two-Way Avoidance

The animals have to move from a compartment A to another compartment B in order to avoid the electric shock (0.8 mA for 15 seconds) which is alternately applied either to the floor of cage A or to the floor of cage B. An audio conditioned stimulus (300 Hz) enables them to avoid this shock provided they react within a period of 6 seconds (duration of the conditioned stimulus and the interval). The training takes place over five consecutive days at a rate of one session per day. Each session is made up of 15 trials. The interval between the trials is 50 seconds. The test is introduced one month after irradiation. Four repeat sessions are proposed, 2½, 4½, 8 and 9 months after irradiation. The number of avoidances is recorded.

Statistics

The raw individual data are used to calculate the mean values, the standard deviations, the standard errors in the mean (sem), the group sizes and the Student t values for paired series.

Results

Percentage Avoidance

The intragroup comparison (Table IV) shows a significant difference as regards the change in the percentage avoidance within the treated irradiated group (30.83% vs 49.170%, p=0.05, degree of freedom (dof)=7) between the third repeat of the test (D257) and the one (fourth) applied after 6 injections of liposomal Cu/Zn SOD (D283). This change was not observed in the control irradiated group (36.19% vs 34.29%, p=0.83) for the same period.

TABLE IV

| Rat no. | D257 | D283 | D257–D283 |
|---|---|---|---|
| LIPSOD | | | |
| 1 | 6.67 | 6.67 | 0.00 |
| 5 | 6.67 | 40.00 | 33.33 |
| 8 | 33.33 | 53.33 | 20.00 |
| 9 | 33.33 | 20.00 | –13.33 |
| 12 | 40.00 | 46.67 | 6.67 |
| 13 | 20.00 | 66.67 | 46.67 |
| 16 | 93.33 | 100.00 | 6.67 |
| 18* | 13.33 | 60.00 | 46.67 |
| mean | 30.832 | 49.168 | 18.355 |
| standard deviation | 28.269 | 28.715 | 22.182 |
| sem | 9.99 | 10.152 | 7.843 |
| n | 8 | 8 | 8 |
| Student t | | | 2.338 |
| p= | | | 0.052 |
| CONTROLS | | | |
| 2 | 40.00 | 40.00 | 0.00 |
| 6 | 6.67 | 0.00 | –6.67 |
| 7 | 53.33 | 33.33 | –20.00 |
| 10 | 26.67 | 33.33 | 6.67 |
| 11 | 26.67 | 66.67 | 40.00 |
| 14 | 40.00 | 40.00 | 0.00 |
| 19* | 60.00 | 26.67 | –33.33 |
| mean | 36.191 | 34.286 | –1.906 |
| standard deviation | 17.992 | 19.788 | 23.001 |
| sem | 6.801 | 7.479 | 8.69 |
| n | 7 | 7 | 7 |
| Student t | | | 0.219 |
| p= | | | 0.834 |

*3.5 Gy/day

Conclusion

The post-irradiation curative effect of liposomal Cu/Zn SOD is found to be of significant importance in terms of the parameter studied during the fourth repeat (D283) of two-way avoidance. The improvement in the expression of a deficient response induced by irradiation is comparable to the protective effect observed previously (Example 1).

Unexpectedly, the treatment with SOD improves the brain functions of rats which have become chronically deficient under the effect of irradiation.

In fact, an irradiation of 30 Gy in 10 sessions over 12 days substantially and chronically impairs the cognitive brain functions of old rats without causing morphological anomalies of the brain in optical microscopy, whereas subcutaneous injections of SOD 9 months after irradiation substantially improve the brain functions of the rats, making them comparable to those of the non-irradiated control rats.

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

We claim:

1. A method of treating or preventing cognitive brain function disorders that result from cerebral damage or injury, comprising the step of administering an effective amount of a SOD preparation to a patient in need thereof.

2. The method of claim 1, wherein the cognitive brain function disorder results from direct cerebral damage or injury.

3. The method of claim 1, wherein the cognitive brain function disorder results from indirect cerebral damage or injury.

4. The method of any of claims 1 to 3, wherein the SOD preparation has an extended duration of action.

5. The method of claim 4, wherein the SOD preparation is administered subcutaneously.

6. The method of claim 4, wherein the SOD preparation is administered parenterally.

7. The method of claim 4, wherein the preparation is administered orally.

8. The method of claim 4, wherein the preparation is administered at a daily dose of about 0.03 mg/kg to about 0.08 mg/kg.

9. The method of claim 4, wherein the SOD preparation with an extended duration is selected from the group consisting of a liposomal SOD preparation, Cu/Zn SOD, Mn SOD, Fe SOD, recombinant human Mn SOD, a SOD/polyethylene glycol conjugate, a SOD polymer and a SOD copolymer.

10. A method of treating or preventing cognitive brain function disorders that results from cerebral damage or injury and that interferes with the acquisition of training, comprising the step of administering an effective amount of a SOD preparation to a patient in need thereof.

11. The method of claim 10, wherein the cognitive brain function disorder is caused by direct cerebral damage.

12. The method of claim 11, wherein the direct cerebral damage is caused by irradiation of the patient's head.

13. The method of claim 10, wherein the cognitive brain function disorder is caused by indirect cerebral damage.

* * * * *